United States Patent [19]
Scott

[11] Patent Number: 6,067,019
[45] Date of Patent: *May 23, 2000

[54] BED EXIT DETECTION APPARATUS

[75] Inventor: Thomas E. Scott, Indianapolis, Ind.

[73] Assignee: Hill-Rom, Inc., Batesville, Ind.

[*] Notice: This patent issued on a continued prosecution application filed under 37 CFR 1.53(d), and is subject to the twenty year patent term provisions of 35 U.S.C. 154(a)(2).

[21] Appl. No.: 09/031,749

[22] Filed: Feb. 27, 1998

Related U.S. Application Data

[63] Continuation-in-part of application No. 08/755,961, Nov. 25, 1996, Pat. No. 5,808,552.

[51] Int. Cl.[7] .................................................. G08B 23/00
[52] U.S. Cl. ..................................... 340/573.4; 340/573.5; 340/562; 340/686.1
[58] Field of Search ............................. 340/573.4, 573.5, 340/562, 572.2, 572.4, 686.1; 600/483, 484; 5/940

[56] References Cited

U.S. PATENT DOCUMENTS

| | | |
|---|---|---|
| 3,533,095 | 10/1970 | Collins . |
| 3,752,144 | 8/1973 | Weigle, Jr. ............................... 600/587 |
| 3,890,958 | 6/1975 | Fister el al. ............................... 600/527 |
| 4,175,263 | 11/1979 | Triplett et al. ........................ 340/573.4 |
| 4,320,766 | 3/1982 | Alihanka et al. ........................ 340/562 |
| 4,474,185 | 10/1984 | Diamond ................................ 600/535 |
| 4,539,560 | 9/1985 | Fleck et al. ........................... 340/573.4 |
| 4,633,237 | 12/1986 | Tucknott et al. ...................... 340/573.4 |
| 4,796,013 | 1/1989 | Yasuda et al. ........................... 340/562 |
| 4,934,468 | 6/1990 | Koerber, Sr. et al. ................... 177/144 |
| 4,951,032 | 8/1990 | Langsam ................................ 340/552 |
| 4,953,244 | 9/1990 | Koerber, Sr. et al. ....................... 5/600 |
| 5,140,309 | 8/1992 | Gusakov ............................... 340/573.4 |
| 5,144,284 | 9/1992 | Hammett ............................... 340/573.1 |
| 5,170,364 | 12/1992 | Gross et al. ........................... 702/139 |
| 5,184,112 | 2/1993 | Gusakov ............................... 340/573.1 |
| 5,235,319 | 8/1993 | Hill et al. ............................. 340/573.4 |
| 5,253,656 | 10/1993 | Rincoe et al. ........................... 600/595 |
| 5,276,432 | 1/1994 | Travis .................................... 340/573.4 |
| 5,353,012 | 10/1994 | Barham et al. ...................... 340/573.4 |
| 5,393,935 | 2/1995 | Hasty et al. ............................... 177/45 |
| 5,410,297 | 4/1995 | Joseph et al. ........................ 340/573.4 |
| 5,446,391 | 8/1995 | Aoki et al. ............................... 340/562 |
| 5,448,996 | 9/1995 | Bellin et al. ............................ 600/574 |
| 5,459,452 | 10/1995 | DePonte ............................... 340/573.5 |
| 5,471,198 | 11/1995 | Newham ............................... 340/573.4 |
| 5,479,939 | 1/1996 | Ogino .................................... 600/595 |
| 5,543,777 | 8/1996 | Vane et al. ............................... 340/514 |
| 5,602,734 | 2/1997 | Kithil ....................................... 701/45 |
| 5,633,627 | 5/1997 | Newham ............................... 340/573.4 |
| 5,697,366 | 12/1997 | Kimball et al. ......................... 600/309 |
| 5,699,038 | 12/1997 | Ulrich, et al. ...................... 340/286.07 |
| 5,791,344 | 8/1998 | Schulman et al. ...................... 600/347 |
| 5,800,480 | 9/1998 | Augustine, et al. ...................... 607/96 |
| 5,802,479 | 9/1998 | Kithil et al. ............................... 701/45 |
| 5,808,522 | 9/1998 | Wiley, et al. ............................ 333/187 |
| 5,808,552 | 9/1998 | Wiley et al. ........................ 340/573.4 |

FOREIGN PATENT DOCUMENTS

| | | | |
|---|---|---|---|
| 0 441 381 A1 | 8/1991 | European Pat. Off. ............ | 340/573.4 |
| WO 89/02635 | 3/1989 | WIPO ................................ | 340/545.3 |

*Primary Examiner*—Jeffery A. Hofsass
*Assistant Examiner*—Van T. Trieu
*Attorney, Agent, or Firm*—Bose McKinney & Evans

[57] ABSTRACT

A patient detection system including a plurality of sensors located adjacent the support surface and each sensor having an output signal variable in response to the change detected by the sensor. A processor monitors the output signals and provide an indication of change of position of the body relative to the support surface and to individually recalibrate each of the plurality of sensors. The automatic recalibration occurs upon sensing a substantial change due to an item being moved onto the surface. The processor may also sense changes in the support surface and recalibrate each of the sensors upon a detection of change in the support surface. The processor recalibrates all of the sensors for small changes existing for a pre-determined duration and for all large changes. The processor recalibrates all of the processors for a combination of changes in less than all of the sensors from the previous calibration for each sensor.

22 Claims, 5 Drawing Sheets

BED EXIT DETECTION APPARATUS

CROSS-REFERENCE

This is a continuation-in-part of U.S. patent application Ser. No. 08/755,961 filed Nov. 25, 1996, now U.S. Pat. No. 5,808,552.

BACKGROUND AND SUMMARY OF THE INVENTION

The present invention relates to patient-support devices and particularly to a patient detection system for detecting the presence of a patient on a patient-carrying surface of the patient-support device. More particularly, the present invention relates to a device for detecting the dielectric constant within a detection space adjacent to the patient-carrying surface, the dielectric constant corresponding to the presence or absence of the patient in the detection space, the device providing a signal in response to the dielectric constant within the detection space, the signal indicating the presence or absence of the patient in the detection space thereby indicating the presence or absence of the patient on the patient-carrying surface.

It is sometimes desirable to monitor the whereabouts of a patient, particularly when a doctor or other care giver has ordered that the patient remain on a patient-support device such as a hospital bed, a stretcher, or other device for carrying the patient. Several devices have been developed for detecting a patient exit from a patient-support device. For example, U.S. Pat. No. 5,276,432 to Travis discloses a bed exit detection mechanism for a hospital bed that relies on signals from load cells coupling the mattress to a frame of the bed. This device uses the weight measured by each load cell to determine whether the center of gravity of the patient is over a predetermined region of the patient-carrying surface of the hospital bed. In addition, U.S. Pat. Nos. 4,934,468 and 4,953,244, each of which are assigned to the assignee of the present invention, disclose a hospital bed having a support frame and a weigh frame mounted on the support frame by load cells.

It is also known to monitor the position of a person by attaching a portion of a transmitter/receiver system to the person being monitored so that when the person and thus the portion of the system attached to the person leaves a designated area, the remaining portion of the system detects the departure of the portion and thus the departure of the person and provides an indication of the person's departure. For example, U.S. Pat. No. 5,519,380 to Edwards discloses a bracelet module that is worn by the monitored person so that when the person and the bracelet module move outside of the monitored volume, an indication of departure is provided.

It is also known to monitor the position of a patient on a bed using bladders or other fluid-carrying devices positioned to lie between the patient and the bed and in fluid communication with a pressure sensor so that the pressure sensor registers a bladder pressure in response to the patient's weight, the bladder pressure indicating the presence or absence of the patient on the bladder. For example, U.S. Pat. Nos. 5,140,309 and 5,184,122, both to Gusakov, each disclose an apparatus including resilient means in the form of a tube, cell or other form of fluid passage adapted to allow fluid such as air to flow from an inlet through the outlet when a passage is not collapsed by the weight of a patient. Indicating means indicate changes in pressure in the fluid supplied by the fluid supplying means, such as when the weight of a patient collapses the passage through the resilient means. By providing resilient means having a plurality of tubes, cells or other fluid passages and separate indicating means for each resilient means, the position of the patient relative to each resilient means can be monitored.

There are also several known systems that include sensors positioned to lie beneath the patient and that provide electrical signals in response to the weight detected by the sensor so that an output signal indicating a significant change of weight acting against the sensor indicates movement of the patient to a position away from the sensor or to a position on top of the sensor. For example, U.S. Pat. Nos. 4,179,692 to Vance; 5,253,656 to Rinco et al.; 5,353,012 to Barham et al.; and 4,638,307 to Swartout disclose systems each of which include a sensor that provides an output signal in response to a change in the weight acting against the sensor.

Capacitive sensors that provide an output signal in response to the change in weight acting against the sensor are also well known. For example, U.S. Pat. Nos. 5,410,297 to Joseph et al.; 5,235,319 to Hill et al.; and 3,991,746 to Hannah each disclose patient monitoring systems employing capacitive sensors that provide a signal in response to the weight acting against the sensor.

Finally, it is also known to provide capacitive motion sensors for monitoring the movements of a person and even for measuring respiration, heartbeat, and body position of the person. For example, U.S. Pat. Nos. 4,320,766 to Alihanka et al. and 5,448,996 to Bellin et al. each disclose patient monitors including capacitive sensors. The device disclosed by the Alihanka patent can indicate that movement has occurred but cannot indicate what movement occurred or the position of the body when no movement is occurring, and the Bellin patent likewise can indicate movement but not position of the patient or that a patient has exited the bed. Monitoring the position of a patient on the support surface and determining that vacation of the bed by the patient is imminent, is shown in U.S. Pat. No. 4,633,237. An array of pressure sensitive capacitive on-off switches are used.

Recent improvements in bed mattress designs have significantly reduced peak interface pressure between the patient and the mattress by maximizing the area over which the weight of the patient is distributed rather than concentrating the interface pressure at points along the patient, for example, the patient's head, shoulder blades and heels. In addition, recent patient population data indicates that patient-s in general weigh less than in the past. Patient detection systems that rely on the weight of the patient to allow the sensor to detect the patient are rendered less effective as mattresses become more efficient at distributing the weight of the patient across the surface of the mattress and as the weight of the patient decreases. In addition, while it is desirable to minimize the interface pressure of high interface pressure points between the patient and the mattress by distributing the weight of the patient across the mattress, for example, by using mattresses including air bladder supports, interposing a sensor between the top surface of the mattress and the patient significantly reduces the effectiveness of the mattress at distributing the weight of the patient. In addition, for applications in which it is advantageous to keep the patient dry and maintain the temperature of the patient at a desired temperature through the use of a "low air loss" mattress that allows a very small amount of air to escape the mattress and blow on the patient, interposing a sensor between the patient and the mattress reduces the effectiveness of the low air loss feature.

What is needed is a sensor that can sense the position of a patient relative to a patient-carrying surface of a patient-support device that can be positioned to lie away from the patient allowing the sensor to be placed away from the patient-carrying surface. In addition, the sensor should not require the attachment of a portion of the system to the patient. In addition, the sensor should detect the presence of a patient within a window of detection that can be shaped through the use of multiple sensing elements or through the use of a shape sensing element in order to achieve a desired level of detail of detection so that, if desired, a care giver can determine both the position of the patient on the patient-carrying surface as well as the general outline of the patient's body on the patient-carrying surface in order to better monitor the patient.

According to the present invention, an apparatus is provided for detecting the presence or absence of a patient adjacent to a patient-carrying surface of a patient-support device. The apparatus includes a first sensing element spaced apart from the patient-carrying surface. The first sensing element defines a first detection space adjacent to the patient-carrying surface and provides a first input signal in response to the dielectric constant within the first detection space. The apparatus also includes a second sensing element spaced apart from the patient-carrying surface. The second sensing element defines a second detection space adjacent to the patient-carrying surface and provides a second input signal in response to the dielectric constant within the second detection space. A control unit provides an output signal indicating the presence or absence of the patient within the first detection space in response to the first input signal and within the second detection space in response to the second input signal.

The patient detection system can include one or more sensing elements. When a plurality of sensing elements are provided, the sensing elements can be spaced apart to define a plurality of separate, spaced-apart detection spaces and the care giver can monitor the position of the patient by monitoring the signals from each sensing element. It can be seen that by increasing the number of sensing elements in the patient detection system, the care giver can monitor the position of the patient with an increasing level of detail.

The patient detection system includes a plurality of sensors located adjacent the support surface. Each sensor having an output signal variable in response to the change detected by the sensor. A processor is provided having inputs of the output signals from the sensors. The processor monitors the output signals and provide an indication of change of position of the body relative to the support surface and to individually recalibrate each of the plurality of sensors. The automatic recalibration occurs upon sensing a substantial change due to an item being moved onto the surface. This change may be a body moving onto the surface. The processor may also sense changes in the support surface and recalibrate each of the sensors upon a detection of change in the support surface. This would accommodate for changes of pressure in a fluid support surface. The processor recalibrates all of the sensors for small changes existing for a pre-determined duration and for all large changes. The processor recalibrates all of the processors for a combination of changes in less than all of the sensors from the previous calibration for each sensor.

Wherein the support surface can be articulated, the system also includes a position sensor having an output couple the processor. The processor automatically recalibrates the system response to a change in the position of the articulated elements. The processor include an output coupled to a communication port for providing a nurse call system or other remote locations with an indication of change of the position of the body relative to the support surface.

A method according to the present invention of calibrating a plurality of sensors located adjacent the support surface comprises determining an initial calibration value for each sensor. Next, a determination of a change of signal of each sensor from its initial calibration is determined. Each of the plurality of sensors are individually recalibrated when a predetermined set of changes of the individual sensor signals has been determined. The predetermined set of changes may include, if a group of sensors, less than all of the sensors, each have a change above a first value. Also, the set may include if a group of sensors, less than all of the sensors, in total have changes above a second value.

While the patient detection system can provide information relative to the position of a patient on a sleeping surface of a bed, the patient detection system in accordance with the present invention can also be used with other patient-support devices such as stretcher, operating tables, chairs, and the like. For example, a chair including side-by-side first and second sensing elements beneath the seat cushion and side-by-side third and fourth sensing elements behind the back cushion can be used to provide the care giver with detailed information about the patient's posture and positioning on the chair.

Additional objects, features, and advantages of the invention will become apparent to those skilled in the art upon consideration of the following detailed description of preferred embodiments exemplifying the best modes of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 4:
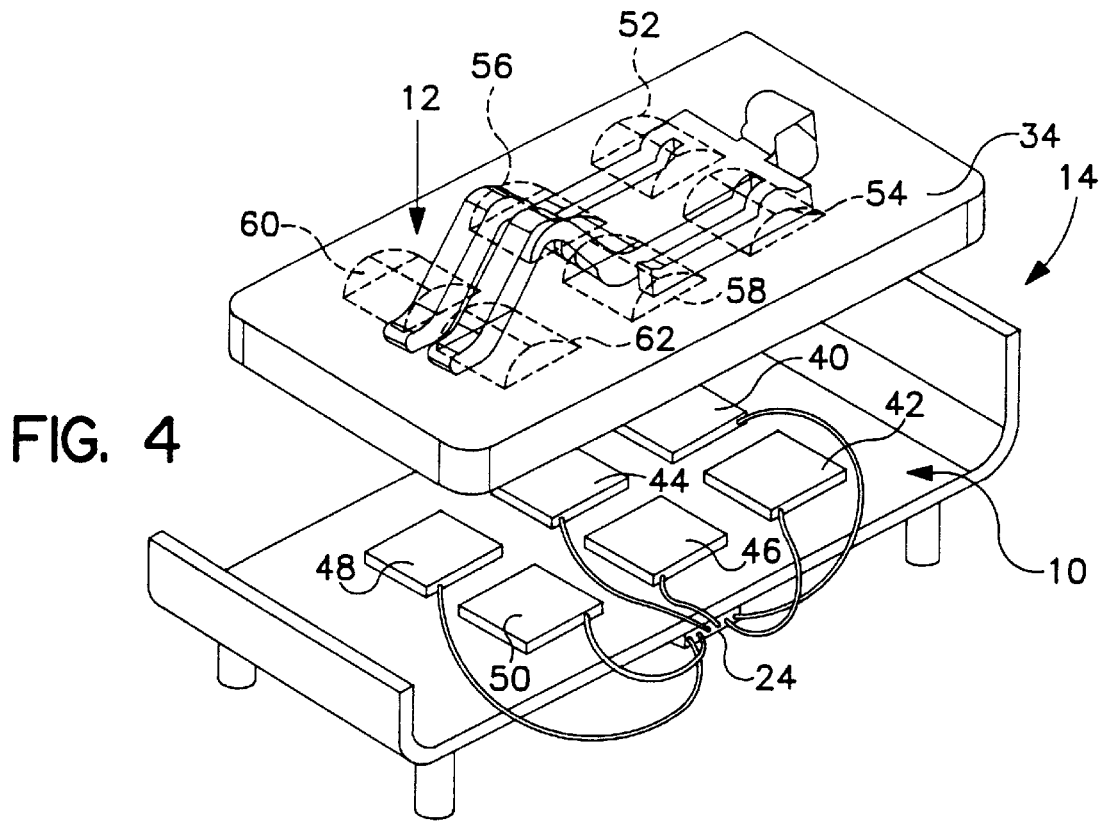
FIG. 4 is a view similar to FIG. 2 showing a plurality of sensing elements in order to provide detailed information related to the position of the patient on the patient-carrying surface.
Figure 5:
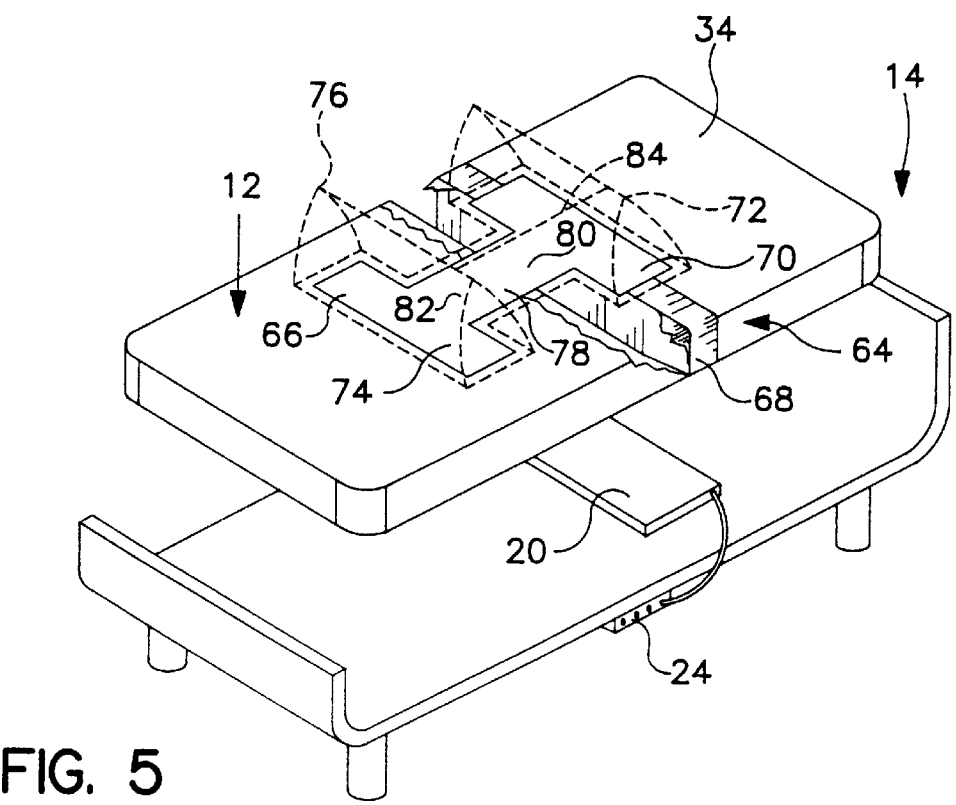
FIG. 5 is a view similar to FIG. 4 showing a single sensing element beneath the mattress and a booster element including an H-shaped plate on the patient-carrying surface and a coupler electrically coupling the plate to the sensing element.
Figure 6:
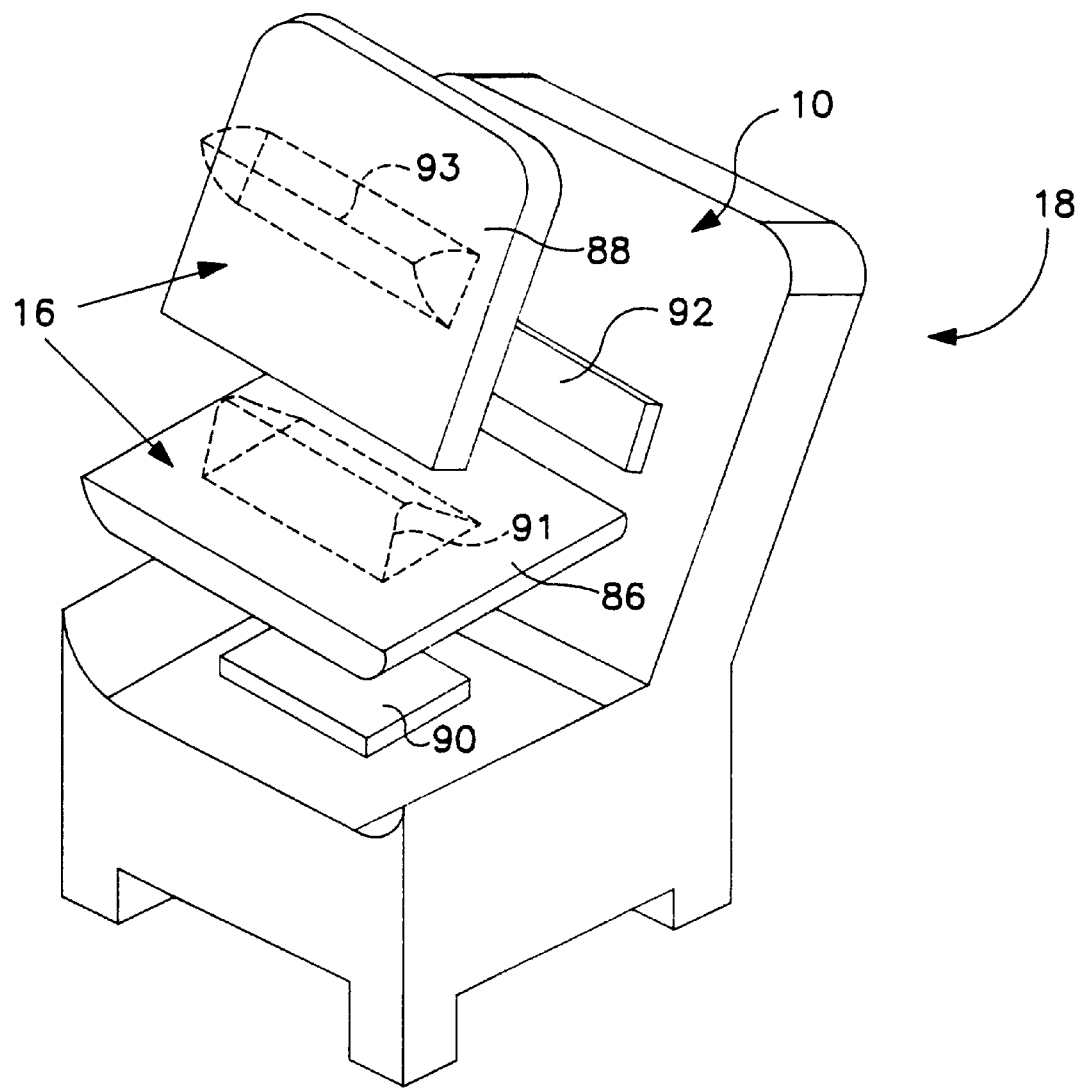
FIG. 6 is an exploded perspective view of a chair including a patient detection system in accordance with the present invention showing a first sensing element positioned to lie beneath a seat cushion and a second sensing element positioned to lie behind a back cushion so that a care giver can determine whether a patient resting on the patient-carrying surface of the chair is slumping forward, away from the back cushion.
Figure 7:
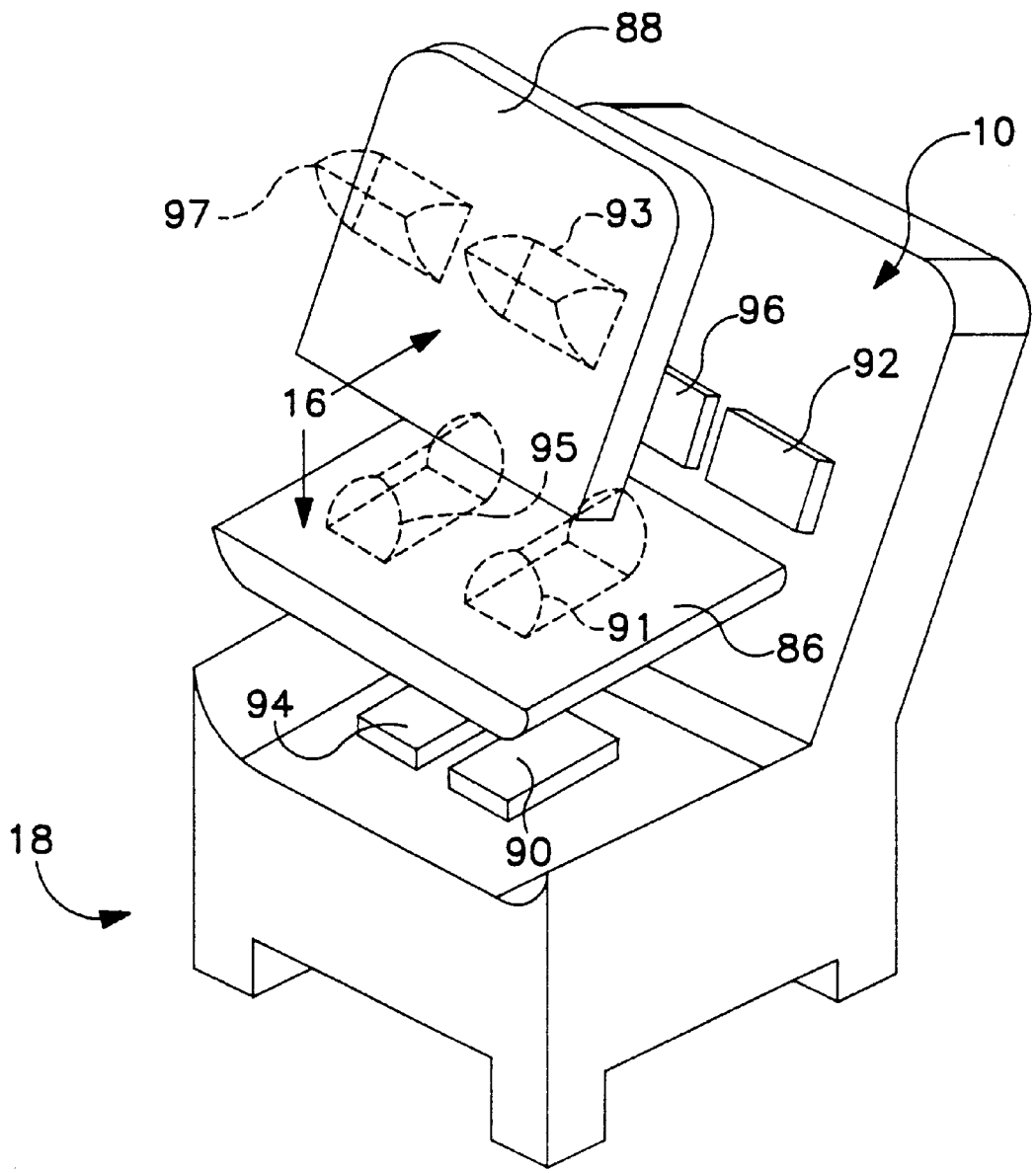
FIG. 7 is a view similar to FIG. 6 showing side-by-side first and second sensing elements beneath the seat cushion and side-by-side third and fourth sensing elements behind the back cushion to provide the care giver with detailed information about the posture and positioning of a patient on the patient-carrying surface of the chair.

A patient detection system 10 in accordance with the present invention can be used to monitor the position of a patient relative to a patient-carrying surface 12 of a bed 14 as shown in FIGS. 1–5, and relative to a patient-carrying surface 16 of a chair 18 as shown in FIGS. 6 and 7. Patient detection system 10 can likewise be used to monitor the position of a patient relative to the patient-carrying surfaces of other patient-support devices including stretchers, operating tables, ambulatory chairs and beds, incubators, radiant warmers, and other patient-support devices relative to which a care giver may wish to monitor the presence or absence and the position of a patient.

Figure 2:
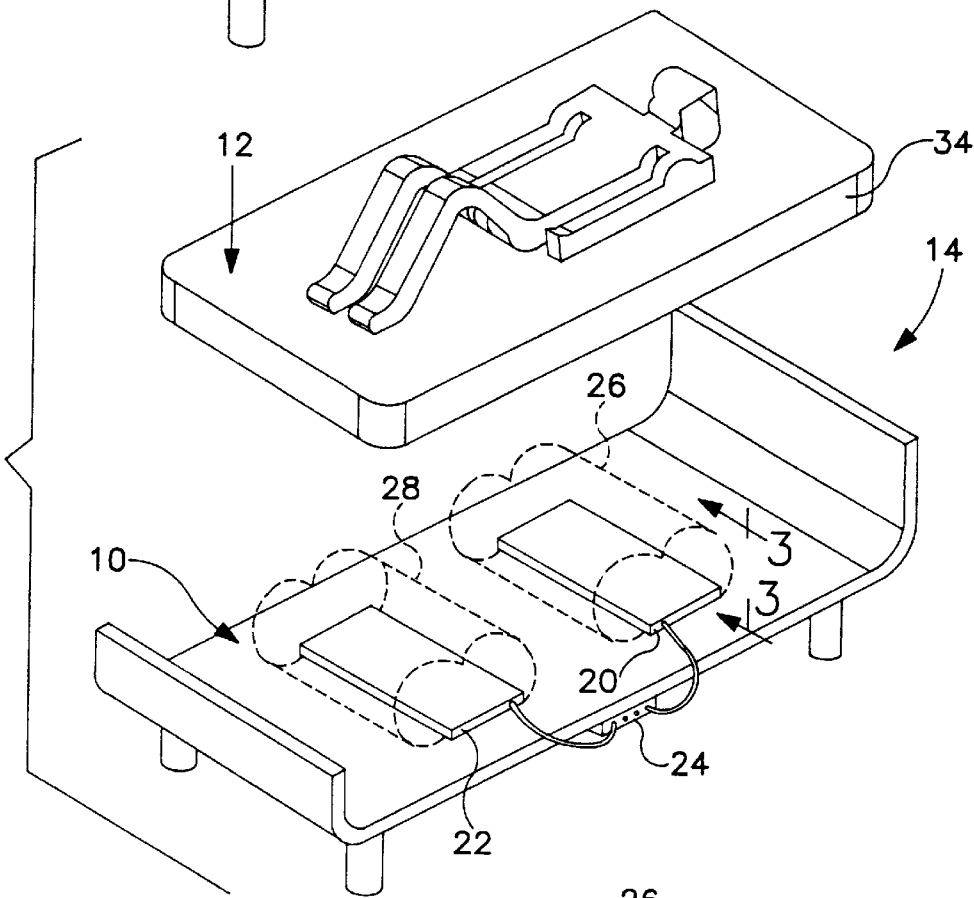
FIG. 2 is an exploded perspective view of the bed of FIG. 1 showing a first sensing element, a second sensing element longitudinally spaced-apart from the first sensing element, the first and second sensing elements being positioned to lie beneath the mattress and each sensing element being coupled to a control unit and providing an input signal thereto in response to the dielectric constant within the detection space.

Patient detection system 10 includes first and second sensing elements 20, 22, as shown, for example, in FIG. 2, that provide first and second input signals, respectively, to a control unit 24 in response to the dielectric constant of the matter within detection spaces 26, 28, respectively. Each sensing element 20, 22 includes an electrical conductor (not shown) and a probe (not shown) that is maintained at ground and potential. Capacitance is measured between the conductor and the probe and first and second input signals correspond, respectively, to the measured capacitance in first and second detection spaces 26, 28, respectively. The preferred sensing elements as described in this document are activated and read by a control unit remote to the sensing elements. The control unit is illustratively a model number HR-60145 manufactured by Gordon Products, Incorporated located in Brookfield, Conn.

Capacitance can be determined using the following relationship:

$$C = \frac{0.22KA}{d}$$

where
C=capacitance;
K=dielectric constant;
A=area of conductors opposing one another; and
d=distance between conductors.

When the area of the conductors opposing one another and the distance between the conductors remains constant, as for sensing elements 20, 22, then the measured capacitance varies proportionally with charges in the dielectric constant in the detection space. The dielectric constant of a human being is significantly different from that of air so that the presence or absence of the patient in detection space 26, 28 can be easily detected by sensing elements 20, 22.

Figure 3:
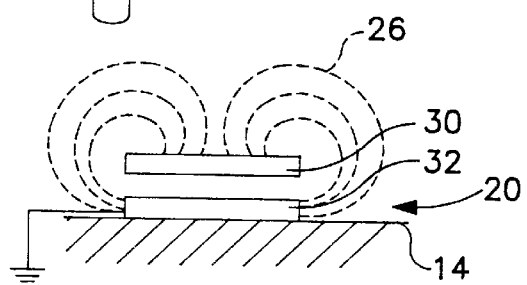
FIG. 3 is a diagrammatic sectional view taken along line 3—3 of FIG. 2 showing a conductor plate of the first sensing element spaced apart from and electrically insulated from a ground plate of the first sensing element.

Each sensing element 20, 22 includes a conductor plate 30, as shown diagrammatically for sensing element 20 in FIG. 3, maintained at an electrical potential other than ground potential, and a ground plate 32 insulated from conductor plate 30 and maintained at ground potential. Capacitance is measured by sensing element 20 in detection space 26 so that as the dielectric constant within detection space 26 changes, such as when a person enters or leaves detection space 26, sensing element 20 detects the new capacitance and provides an input signal to control unit 24 in response to the measured capacitance. Control unit 24 can be configured to provide an output signal indicating the presence or absence of the patient within detection space 26 in response to the input signal from sensing element 20 to alert the care giver. The output signal from control unit 24 can be an electrical signal transmitting information, an audible alarm, a visual alarm, a combination thereof, or any other type of output signal that allows the care giver to monitor the position of the patient on patient-carrying surface 12, 16.

Figure 1:
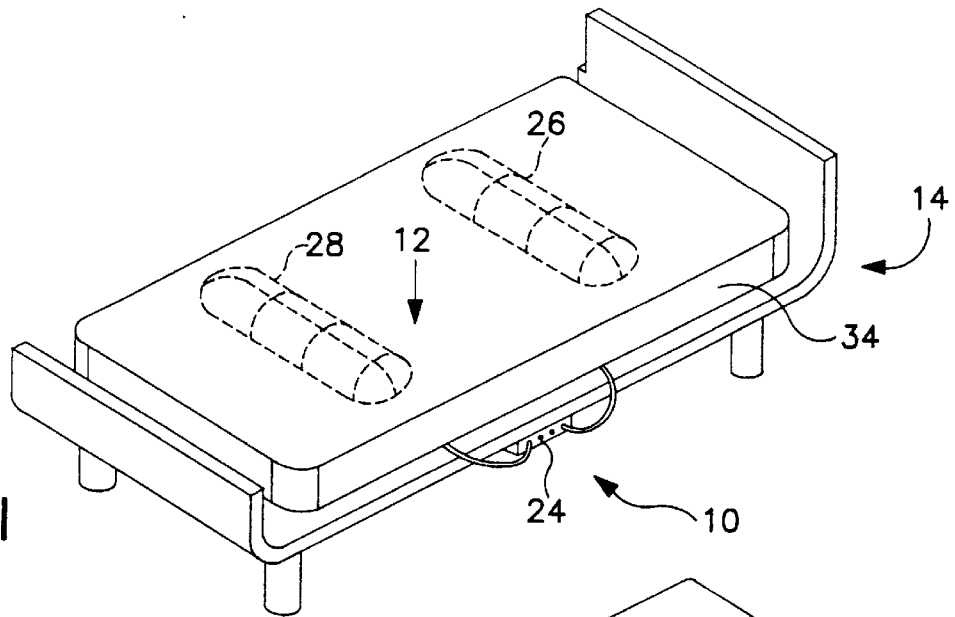
FIG. 1 is a perspective view of a bed including a patient detection system in accordance with the present invention showing a mattress having a patient-carrying surface and a detection space (in phantom) adjacent to the patient-carrying surface.

Patient detection system 10 when used on bed 14 can include first sensing element 20 defining first detection space 26 and second sensing element 22 defining second detection space 28 as shown in FIGS. 1 and 2. While sensing elements 20, 22 can be positioned in any manner desired, it is preferable to position sensing elements 20, 22 beneath a mattress 34 so that sensing elements 20, 22 do not interfere with the operation of mattress 34.

Sensing elements 20, 22 can be placed beneath mattress 34 so that each sensing element 20, 22 extends transversely relative to bed 14 as shown in FIGS. 1 and 2. In addition, sensing elements can be longitudinally spaced apart so that first detection space 26 extends transversely beneath the upper torso of the patient and second detection space 28 is independent of first detection space 26 and extends transversely beneath the thighs or knees of the patient. In this configuration, the care giver would be able to monitor ingress and egress of the patient to and from the patient-carrying surface as well as being able to determine when the patient is lying down and sitting up.

Patient detection system 10 when used on bed 14 can also include a first sensing element 40 defining a first detection space 52, shown diagrammatically over patient-carrying surface 12 of mattress 34 in FIG. 4, a second sensing element 42 defining a second detection space 54, a third sensing element 44 defining a third detection space 56, a fourth sensing element 46 defining a fourth detection space 58, a fifth sensing element defining a fifth detection space 60, and a sixth sensing element 50 defining a sixth detection space 62. Sensing elements 40, 42, 44, 46, 48, 50 are generally identical to sensing elements 20, 22 in principle, however the sizes may vary in order to shape the detection space to conform with the desired shapes of detection spaces 52, 54, 56, 58, 60, 62.

Sensing elements 40, 42, 44, 46, 48, 50 can be transversely spaced apart in a side-by-side arrangement as shown, for example, for sensing elements 40, 42 in FIG. 4 to provide transversely spaced-apart and independent detection spaces 52, 54. Sensing elements 40, 42, 44, 46, 48, 50 can also be longitudinally spaced apart as shown, for example, for sensing elements 42, 46 to provide longitudinally spaced-apart and independent detection spaces 54, 58. Each sensing element 40, 42, 44, 46, 48, 50 provides an input signal to control unit 24 in response to the dielectric constant in each respective detection space 52, 54, 56, 58, 60, 62 and control unit 24 provides an output signal indicating the presence or absence of the patient in each detection space 52, 54, 56, 58, 60, 62 in response to the input signals.

Thus, it can be seen that patient detection system 10 can be configured to provide a variety of degrees of detail about the position of the patient relative to patient-carrying surface 12 by varying the number of sensing elements included in patient detection system 10. For example, if patient detection system 10 includes just one sensing element, the care giver will be able to monitor the output signal from control unit 24 and be able to determine whether or not the patient is present on patient-carrying surface 12. However, if patient detection system 10 includes several sensing elements such as sensing elements 40, 42, 44, 46, 48, 50 as shown in FIG. 4, the care giver is provided with greater detail about the position of the patient on patient-carrying surface 12 so that the care giver can monitor the outline of the patient's body and determine the position that the patient is in. If desired, the care giver could monitor, for instance, the amount of time that a patient spends lying on one side or the other.

Patient detection system 10 can alternatively include a booster element 64 as shown in FIG. 5. Booster element 64 includes a sensing plate 66 positioned to lie on top of patient-carrying surface 12 and an electrically conductive member 68 electrically coupled to sensing plate 66. Conductive member 68 extends around mattress 34 to a position adjacent conductor plate 30 of sensing element 20. Conductive member 68 is preferably positioned within about ¼ inch (0.635 cm) from sensor plate 30 to capacitively couple booster element 64 to conductor plate 30. If desired, conductive member can be positioned under a low dielectric material mattress cover.

By capacitively coupling plate 66 to conductor plate 30 in this manner, plate 66 is maintained at the same electrical potential relative to ground potential as conductor plate 30 so that sensing element measures the capacitance between plate 66 of booster element and ground plate 32 rather than between conductor plate 30 and ground plate 32. As a result, booster element 64 enhances the ability of patient detection system 10 to monitor the patient on patient-carrying surface 12. This enhancement is achieved by enlarging the vertical extent to which the detection space extends above patient-carrying surface 12 and by increasing the sensitivity of the measurement by removing the mass of mattress 34 from the portion of the detection space extending above plate 66.

While illustrated plate 66 has a generally rectangular shape, plate 66 can have almost any shape to provide a detection space having a desired shape. For example, plate 66 can be H-shaped as shown in FIG. 5 having a first portion 70 defining a first portion 72 of the detection space, a second portion 74 defining a second portion 76 of the detection space, second portion 74 being spaced apart from first portion 72. In addition, plate 66 can have a third portion 78 having a first end 80 connected to first portion 70 of plate 66 and a second end 82 longitudinally spaced apart from first end 80 and connected to second portion 74 of plate 66, third portion 78 of plate 66 defining a third portion 84 of the detection space. It can be seen that movement of the patient into or away from any of the portions 72, 76, 84 of the detection space will result in an output signal from control unit 24 indicating the movement of the patient. Thus, plate 66 can be generally rectangular, H-shaped, or any other desired shape in order to provide a detection space having a corresponding desired shape without exceeding the scope of the invention as presently perceived.

Electrically conductive member 68 simply capacitively couples plate 66 to conductor plate 30 of sensing element 20. As such, member 68 can be made from generally any material and in generally any form suitable for use on the patient-support device. For example, member 68 can be a cable connecting plate 66 to plate 30. Likewise, member 68 can be an electrically conducting portion of mattress 34. Preferably, however, member 68 is a metallized mylar band that encircles mattress 34 without interfering with the movement of mattress 34. Thus, it is within the scope of the invention as presently perceived for member 68 to include any electrically conductive member suitable for use on a patient-support device.

Plate 66 can also be made from a variety of materials that are electrical conductors and it is within the scope of the invention as presently perceived to provide plate 66 made from metallized mylar or any other electrically conductive material suitable for use on or near a patient-carrying surface of a patient-support device. While plate 66 and member 68 can be carried on the outside of mattress 34, it is also within the scope of the invention as presently perceived for plate 66 and member 68 to be built-in to mattress 34 and positioned to lie within the mattress cover (not shown).

Although FIGS. 1–5 show patient detection system 10 used on bed 14, it is within the scope of the invention as presently perceived to use system 10 on other patient-support devices including stretchers, operating tables, incubators, infant warmers, ambulatory chairs, other hospital chairs, and any other patient-support device upon which a patient might be carried and for which a care giver may wish to monitor the patient. For example, patient detection system 10 can be used to monitor the position of a patient on patient-carrying surface 16 of chair 18 as shown, for example, in FIGS. 6 and 7.

Chair 18 includes a seat cushion 86 positioned to lie beneath the patient and a back cushion 88 positioned to lie behind the back of the patient. A first sensing element 90 is positioned to lie beneath seat cushion 86 and is configured to define a first detection space 91 over seat cushion 86 adjacent to patient-carrying surface 16 as shown in FIG. 6. A second sensing element 92 is positioned to lie behind back cushion 88 and is configured to define a second deduction space 93 in front of back cushion 88 adjacent to patient-carrying surface 16. First and second sensing elements 90, 92 are substantially similar to sensing element 20 and each provides an input signal to a control unit (not shown) in response to the presence or absence of the patient in detection space 91, 93, respectively. The control unit provides an output signal for use by the care giver indicating the presence or absence of the patient in detection spaces 91, 93 in response to the input signals. The output signal can indicate to the care giver both the presence or absence of the patient on patient-carrying surface 16 and whether the patient is sitting upright or is leaning, falling forward, or falling sideways.

As with bed 14, more detailed information about the patient resting on chair 18 can be provided to the care giver if patient detection system 10 includes additional sensing elements as shown, for example, in FIG. 7. Patient detection system 10 shown in FIG. 7 includes first sensing element 90 defining first detection space 91, second sensing element 92 defining second detection space 93, a third sensing element 94 positioned to lie beneath seat cushion 86 and transversely spaced apart from first sensing element 90, third sensing element 94 defining a third detection space 95 over seat cushion 86 adjacent to patient-carrying surface 16 and transversely spaced apart from first detection space 91, and a fourth sensing element 96 positioned to lie behind back cushion 88 and transversely spaced apart from second sensing element 92, fourth sensing element 96 defining a fourth detection space 97 in front of back cushion 88, adjacent to patient-carrying surface 16, and transversely spaced apart from second detection space 93. Sensing elements 90, 92, 94, 96 are substantially similar to sensing element 20 and each sensing element 90, 92, 94, 96 provides an input signal to a control unit (not shown) in response to the presence or absence of the patient in detection space 91, 93, 95, 97, respectively. The control unit provides an output signal for use by the care giver indicating the presence or absence of the patient in detection spaces 91, 93, 95, 97 in response to the input signals. The output signal can indicate to the care giver both the presence or absence of the patient on patient-carrying surface 16, whether the patient is sitting on both or only one buttock, and whether the patient is sitting in a manner bending their back in an unwanted curvature.

It can be seen that patient detection system 10 can be used to monitor the presence or absence of a patient on patient-carrying surface 12, 16 of a patient-support device. In addition, patient detection system 10 can be configured to provide various levels of detail so that, if desired, the output signal from control unit 24 can indicate not only the presence or absence of the patient, but also the position of the patient. The sensing elements of patient detection system 10 can be positioned to lie beneath mattress 34 or cushions 86, 88 so that the sensing elements do not interfere with the operation of mattress 34 or cushions 886, 88 or interfere with the patient's comfort. Finally, the sensing elements can be shaped or the number and positions of the sensing elements can be varied in order to shape the detection space as desired.

Figure 8:
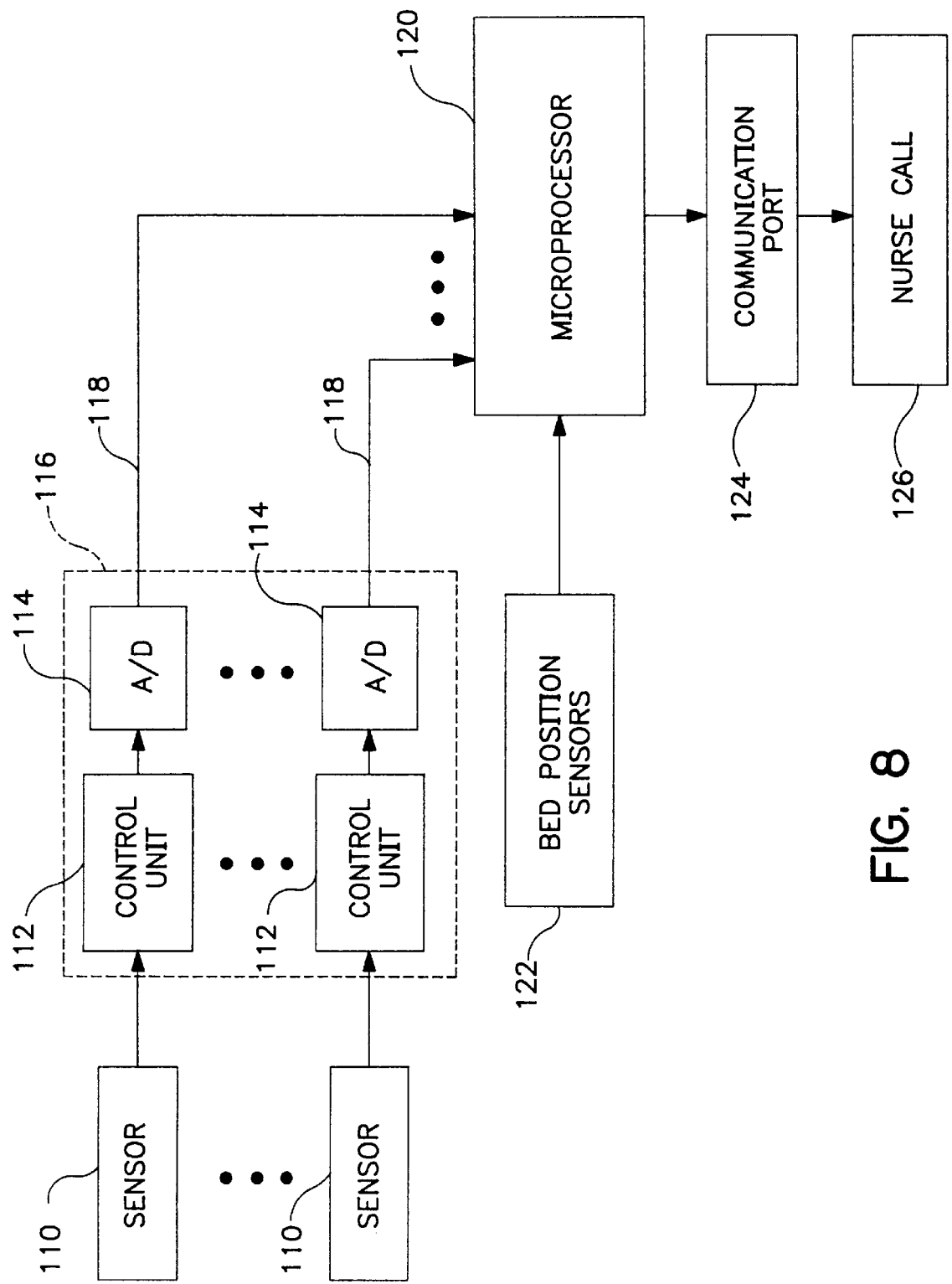
FIG. 8 is a block diagram of another embodiment of the present invention in which sensor outputs are coupled to a computer for processing the sensor signals to provide a bed exit indication to an appropriate nurse call system.

Another embodiment of the present invention is illustrated in FIG. 8. In this embodiment, an array of capacitance sensing elements 110 is provided as discussed above with reference to FIGS. 1–7. Any desired number of sensing elements 110 can be used to provide a sensing array below the mattress 34. In the FIG. 8 embodiment, each sensing element 110 is coupled to a control unit 112 which provides an analog output signal in which the output voltage varies continuously with change in capacitance from the sensors 110. Illustratively, control units 112 are a Model PCA25 available from Gordon Products, Incorporated.

An output from each control unit 112 is coupled to an analog-to-digital (A/D) convertor 114. The separate control units 112 and A/D convertors 114 may be included on a single control board 116. Each sensor output from its associated A/D convertor 114 on line 118 is coupled to a microprocessor 120. Microprocessor 120 also receives an input from bed position sensors 122 which indicates the position of an articulating bed supporting the mattress. An output from microprocessor 120 is coupled to a communication port 124. Illustratively, communication port 124 is a COMposer™ on-line kit available from Hill-Rom, Inc. Communication port 124 is coupled to a nurse call system 126. Nurse call system 126 includes active communications for communicating with the hospital network or a remote network.

In the FIG. 8 embodiment, microprocessor 120 detects variations in capacitances by each sensor 110. Therefore, the microprocessor 120 can calculate a total of all the output values from sensors 110. Microprocessor 120 can also detect each sensor output value. By providing both individual and summed sensor readings, the microprocessor 120 can calibrate itself in response to changes in mattresses, cushions, overlays and other objects added to the patient support surface. Microprocessor 120 can store a new base or reference capacitance reading for comparison at any time. This automatic calibration can be activated with or without the patient located in the bed or chair. Again, the microprocessor 120 detects capacitance readings from all the sensors 110 and then sets a base capacitance value for comparison with the patient located in the bed or chair.

An example of the microprocessor operation will be described with respect to a five sensor system having four corner sensors and one center sensor. This would be the equivalent of FIG. 4 wherein the sensors 44 and 46 are combined as a single sensor in the center of the bed instead of a pair along the sides. In the following examples, the total increase of a capacitance on all five of the sensors is 225 units for a 200 pound patient laying centered on the bed. The values in the example would vary depending upon the mass of the patient. The microprocessor may include a set routine to measure the total mass of the patient on the bed and adjust the threshold limits depending upon the mass. This would be useful, for example, if a patient is closer to 100 pounds or under 50 pounds, for children and infants. The following definitions are used in the examples.

COR=the change of the four corner sensors
H=the change of the two head sensors
L=the change of the two left sensors
R=the change of the two right sensors
T=the change of the two thigh sensors
A=the change in all five sensors
HR=the change in the right head sensor
HL=the change in the left head sensor
TR=the change in the right thigh sensor
TL=the change in the left thigh sensor
CEN=the change in the center sensor
( ) indicates a loss in capacitance since the last calibration It is desirable to continuously recalibrate the system for small changes which persist for a preset amount of time. These generally relate to shifting of the body on the surface versus a body entering or leaving the support surface. The following are two examples of predetermined set of conditions which must exist for at least two seconds before each of the individual sensors will be recalibrated from its initial calibration:

1. Three of the following must be true:
   6>(HR)>=2
   6>(HL)>=2
   6>(TR)>=2
   6>(TL)>=2
   {(CEN)<16} OR [CEN<6]
and none of the sensors HR, HL, TR, TL or CEN can have changes more than 6 units. [(X) OR X<6 where X is HR, HL, TR, TL and CEN]

2. COR>=10
and none of the sensors HR, HL, TR, TL or CEN will have changed more than 4 units [(X)<4 OR<4 where X is HR, HL, TR, TL, and CEN]

Since the microprocessor 120 receives an output from bed positions sensors 122, the microprocessor 120 can be programmed to recalibrate the system automatically if a head section of the bed is raised or lowered, or if a seat back position in a chair is changed. The microprocessor 120 can be recalibrated based upon any movement of the bed or chair, if desired.

The control system of FIG. 8 can sense changes in the mattress 34 and automatically recalibrate the system to adjust for the mattress changes. In addition, the FIG. 8 embodiment provides the ability to determine if an active surface, such as a low air loss mattress, has ceased to function properly. For instance, if an air mattress fails, the patient will move much closer to the sensors 110 below the mattress. Microprocessor 120 detects this large increase in capacitance and provides an indication of mattress problems to the nurse or to the manufacturer at a remote location.

The system of FIG. 8 also permits closer monitoring of patient movement on the mattress. Since the output of sensors 110 varies constantly with capacitance changes, microprocessor 120 can detect subtle movements of a patient within the detection regions of sensors 110. Therefore, the microprocessor 120 can detect shifting of the patient's body even if the patient has not moved out of a sensor detector region.

Using the previous five sensor example, the value of the individual sensors may provide a warning that the patient's body has shifted on the bed to such a position as to warn that an exit may be about to occur. The following are five examples of changes of value of the sensors which would predict a possible exit.

1. TR>=25 AND (CEN)>16
2. TL>=25 AND (CEN)>16
3. L>=32 AND (R)>20 AND (CEN)>16
4. R>=32 AND (L)>20 AND (CEN)>16
5. T>=30 AND (CEN)>10

The first two example by measuring the left or right thigh is for a patient who is positioning themselves to sit on the edge of the lower part of the bed before exiting. The last example 5 is when a patient is attempting to exit the foot of the bed. The same condition can be used for the head of the bed but is not necessarily practical since there is usually a headboard. Preferably, the system would provide two different modes of enunciation for a bed exit and for a prediction of a bed exit such that nurses and other can determine the urgency of the signal.

Microprocessor 120 can be programmed to recalibrate the system upon any substantial capacitance changes. In this way, if the system is activated when the patient is not located on the support surface, microprocessor 120 automatically recalibrates the system when the patient lies on the support surface. In another words, the microprocessor 120 detects the large capacitance change when the patient enters the bed or chair and then automatically recalibrates the system based upon the new capacitance values received from sensors 110.

Using the format of the previous example for five sensors, a bed exit may be detected and the system recalibrated using the following four examples. It should also be noted that if the change is in a positive manner, the system will be recalibrated indicating that a person has entered the bed.

1. The following must all be true:
    (COR)>=10
    (HR)<4 OR HR<4
    (HL)<4 OR HL<4
    (TR)<4 OR TR<4
    (TL)<4 OR TL<4
    (CEN)>4
    (H)>=5
2. The following must all be true:
    (COR)>=20
    (CEN)>=12
    (L)<15 OR L<15
    (R)<OR R<15
3. (A)>=75
4. (T)>=16 AND (CEN)>=25

Although the control system of FIG. 8 and the operation of the microprocessor has been described with respect to the capacitive sensors, other sensors which provide a varying signal either digital or analog, depending upon a change that it senses it may be used.

Although the invention has been described in detail with reference to certain preferred embodiments, variations and modifications exist within the scope and spirit of the invention as described and defined in the following claims.

I claim:

1. An apparatus for detecting and monitoring a body adjacent a support surface, the apparatus comprising:
    a plurality of sensors located adjacent the support surface, each sensor having an output signal being variable in response to change detected by its corresponding sensor; and
    a processor having inputs for receiving the output signals from the sensors, the processor monitoring individually the output signals from each sensor to provide an indication of change of position of the body relative to the support surface and to individually recalibrate each of the plurality of sensors.

2. The apparatus of claim 1, wherein the processor automatically recalibrates the sensors upon sensing substantial change due to an item being moved onto the support surface.

3. The apparatus of claim 1, wherein the support surface is located on an articulating bed having a bed position sensor, the bed position sensor having an output coupled to the processor, the processor automatically recalibrating the system in response to changes in bed position.

4. The apparatus of claim 1, wherein the processor detects when a body moves onto the support surface and the processor automatically recalibrating the system upon detection of the body moving onto the support surface.

5. The apparatus of claim 1, wherein the processor includes means for monitoring movement of the body within a detection region of each sensor.

6. The apparatus of claim 1, wherein the processor includes an output coupled to a communication port for providing a nurse call system with an indication of change of position of the body relative to the support surface.

7. The apparatus of claim 1, wherein the processor senses changes in the support surface and the processor recalibrates each of the plurality of sensors upon detection of changes in the support surface.

8. The apparatus of claim 7, wherein the processor includes an output coupled to a communication port, the processor transmitting an output signal through the communication port to a remote location upon detection of changes in the support surface.

9. The apparatus of claim 7, wherein the support surface is supported by a fluid.

10. The apparatus of claim 1, wherein the processor recalibrates all the sensors for small capacitive changes existing for a predetermined duration and for all large changes.

11. The apparatus of claim 1, wherein the processor recalibrates all the sensors for a predetermined set of individual changes from the previous calibration for each sensor.

12. A apparatus of claim 11, wherein the predetermined set of changes includes if a group of sensors, less than all the sensors, each have changes above a first value.

13. A apparatus of claim 12, wherein the predetermined set of changes includes if a group of sensors, less than all the sensors, in total have changes above a second value.

14. A apparatus of claim 11, wherein the predetermined set of changes includes if a group of sensors, less than all the sensors, in total have changes above a second value.

15. The apparatus of claim 1, wherein the plurality of sensors includes four corner sensors and a center sensor.

16. A method of calibrating a plurality of sensors located adjacent support surface in an apparatus for detecting and monitoring a body adjacent the support surface, each sensor providing a varying signal; the method comprising:
    determining an initial calibration value individually for each sensor;

determining a change of the signal of each sensor individually from its initial calibration value; and individually recalibrating each of the plurality of sensors when a predetermined set of changes of the individual sensor signals have been determined.

17. A method of claim 16, wherein the predetermined set of changes includes if a group of sensors, less than all the sensors, each have changes above a first value.

18. A method of claim 17, wherein the predetermined set of changes includes if a group of sensors, less than all the sensors, in total have changes above a second value.

19. A method of claim 16, wherein the predetermined set of changes includes if a group of sensors, less than all the sensors, in total have changes above a second value.

20. A method of claim 16, wherein the predetermined set of changes includes if a group of sensors, less than all the sensors, in total or individually have changes above predetermined values; and including determining a category of mass of body on the support surface and adjusting the predetermined values.

21. A method of claim 20, including individually recalibrating each of the plurality of sensors when a predetermined set of changes of the individual sensor signals have been determined.

22. A method of predicting that a patient is about to exit a support surface using a plurality of sensors located adjacent support surface and an apparatus for detecting and monitoring a body adjacent the support surface, each sensor providing a varying signal; the method comprising:

determining an initial calibration value individually for each sensor;

determining a change of the signal of each sensor individually from its initial calibration value; and predicting an exit when a predetermined set of changes of the individual sensor signals have been determined to indicate a significant shift of the patient on the support surface to one of the edges of the support surface since the last calibration.

* * * * *